United States Patent [19]

Clement et al.

[11] 4,328,707
[45] May 11, 1982

[54] ULTRASONIC IMAGE RECONSTRUCTION METHODS AND APPARATUS

[75] Inventors: Michel Clement, Montigny le Bretonneux; Pierre Alais, Dampierre, both of France

[73] Assignee: Agence Nationale de Valorisation de la Recherche, Neuilly sur Seine, France

[21] Appl. No.: 49,304

[22] Filed: Jun. 18, 1979

[30] Foreign Application Priority Data

Jun. 20, 1978 [FR] France .................................. 78 18424

[51] Int. Cl.³ ............................................. G01N 29/00
[52] U.S. Cl. ......................................... 73/618; 73/626; 128/660
[58] Field of Search ................. 73/597, 599, 606, 618, 73/625, 626; 128/660

[56] References Cited
U.S. PATENT DOCUMENTS

| | | | |
|---|---|---|---|
| 3,936,791 | 2/1976 | Kossoff .................................. | 73/626 |
| 4,070,905 | 1/1978 | Kossoff .................................. | 73/626 |
| 4,074,564 | 2/1978 | Anderson ............................... | 73/618 |
| 4,083,232 | 4/1978 | Heyser et al. ......................... | 73/618 |
| 4,105,018 | 8/1978 | Greenleaf et al. ..................... | 73/597 |
| 4,222,274 | 9/1980 | Johnson ................................. | 72/626 |

*Primary Examiner*—Stephen A. Kreitman
*Attorney, Agent, or Firm*—Larson and Taylor

[57] ABSTRACT

Reconstruction of two-dimensional distribution of attenuation coefficients or sound velocities in a cross-sectional plane of an object is achieved by carrying out a plurality of measurements of absorption or of flight time with ultrasound bursts directed by elementary transmitting probes along several different incidences in the sectional plane. Switching between successive measurements is carried out by electronic scanning, without movement of the individual probes. Focusing of the burst energy transmitted by a group of probes is achieved by applying a same electrical signal to the probes with appropriate delays. The secured signals are stored and, after completion of the scanning, they are combined for computation of the distribution.

14 Claims, 26 Drawing Figures

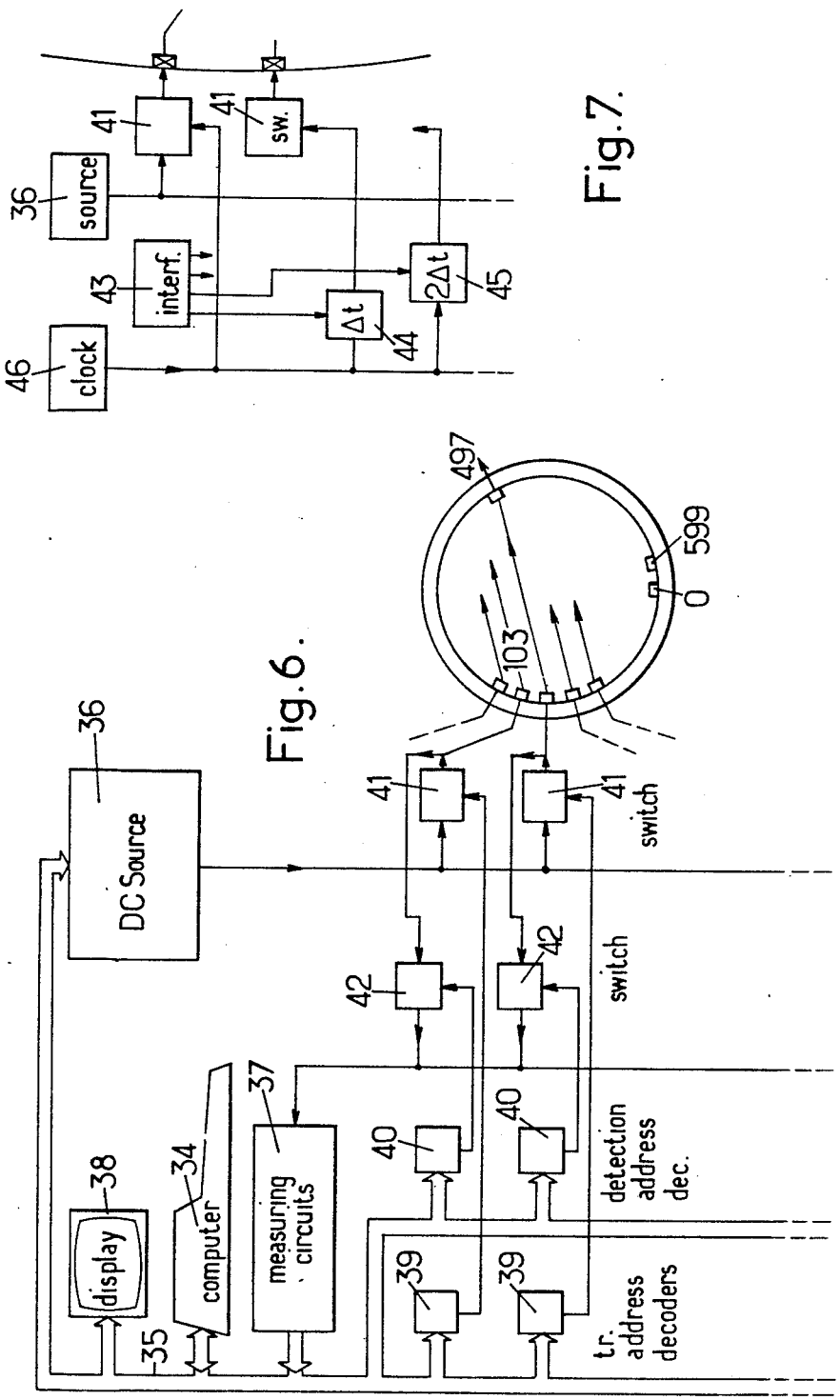

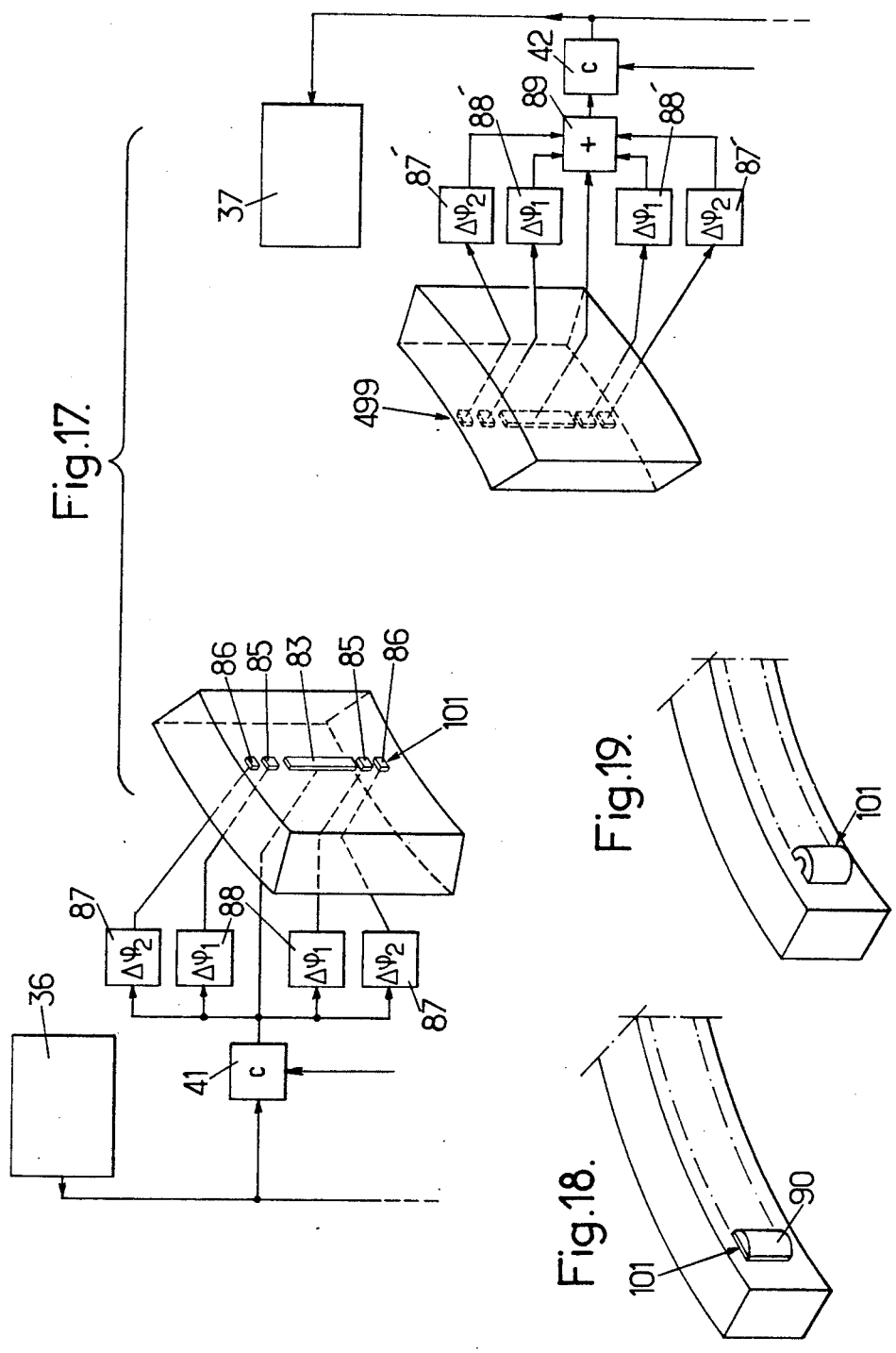

ULTRASONIC IMAGE RECONSTRUCTION METHODS AND APPARATUS

BACKGROUND AND SUMMARY OF THE INVENTION

The present invention relates to ultrasonic image reconstruction tomography and more particularly transverse tomography.

Transverse reconstruction tomography is a technique of obtaining the image of a cross-section of a specimen object in a plane perpendicular to an axis of this object; it comprises the steps of measuring and recording the action of the specimen on a radiation for a large number of radiation paths contained in the cross-section plane and of determining, by means of an algorithm or similar tomographic decoding process, the action of each individual minute zone of the specimen in the cross-section.

Transverse axial tomography has been in use for a long time in medical X imagery. A description thereof may be found in J. AMBROSE, British Journal of Radiology, 46, pp. 1023–1047 (1973). It has also been used in nuclear imagery (see O. E. KUHL and R. S. EDWARDS in "Radiology", 80, pp. 653–662, 1963). Finally, the application of transverse reconstruction tomography to ultrasonic imagery has been recently contemplated (J. F. GREENLEAF et al, "Acoustical Holography", Vol. 6, Plenum Press, New-York, 1975, pp. 71–90).

Tomography of a living organism by ultrasounds is much more attractive that by ionizing radiations, such as X rays and gamma radiation emitted by radio-elements. Moreover, it is possible to carry out not only measures of absorption, but also measures of time of flight, whereby two pieces of information are collected instead of a single one.

On the other hand, most prior art processes of ultrasonic reconstruction tomography have serious shortcomings. The transmitting and receiving probes are moved between two successive measurements or between two successive series of measurements, which leads to a complex and costly apparatus, slow in operation. However, in another prior art technique (U.S. Pat. No. 4,074,564 to ANDERSON), a plurality of fixed transducers are placed in spaced positions about the periphery of the specimen and each transducer in turn may be energized to transmit a burst of ultrasonic energy which is detected by the other transducers. While that technique improves upon the use of movable transducers, it has a low signal/noise ratio and lack of homogeneity of the transmitted beam since the beam should be fan-like with a very large angular aperture.

It is an object of the invention to provide an ultrasonic reconstruction tomography apparatus which does not include moving parts and delivers an improved image of the cross-section of a body.

It is another object of the invention to provide a reconstruction apparatus which achieves electronic scanning as well as electronic transmission and/or detection focusing.

These and other objects of the invention are obtained by carrying out several successive measurements of attenuation, i.e. absorption, time of flight (which is representative of the velocity of sound through the object) or Doppler shift along several paths in the sectional plane. The paths are directed along a plurality of different angular directions to cover substantially the whole cross-section. Detection is made with a plurality of spaced elementary receiving probes some of them only are used for each measurement.

To this end, the invention provides a process for ultrasonic transverse reconstruction tomography. Switching over from one measurement to another is achieved by electronic scanning and without moving the probes. The signals supplied by the elementary receiving probes are stored and the distribution of the absorption coefficients, of the flight speeds and Doppler frequency shifts across the section, is reconstituted by processing the stored data. The ultrasonic beams are focussed by associating several adjacent transmitting probes which cooperate in delivering the same energy burst.

There is also provided an apparatus which comprises a crown of ultrasonic probes spaced angularly apart about an axis intended to be placed perpendicularly to the sectional plane of the object and means for applying to the probes or groups of successive probes energization pulses, so as to create successive ultrasonic beams directed along several different directions in the sectional plane without mechanical movement of the crown, means for collecting the signals received in response to the transmissions by probes or groups of probes, and means for storing the signals provided by the receiving probes, with a view to reconstituting the distribution of absorption coefficients or flight speeds by processing the signals memorized.

Electronic scanning removes the problems associated with movement of the probes. Slow scanning may be carried out, by providing only one measuring circuit which is connected successively to the different receiving probes, or more or less rapid scanning by providing a smaller or greater number of simultaneous measuring channels.

The apparatus also allows concentration of energy at transmission or reception to be achieved by a process which may be qualified as electronic "focusing" or deflection. For transmission of a single "focussed" burst, a group of probes are energized with time or phase lag corresponding to preferential transmission of energy in a given direction. That may be obtained, when probes are energized by a single electric pulse, by means of delay lines. At reception, a comparable technique may be used, using phase-shifters or mixers having a phase signal different from one mixer to the next.

A particularly important field of use of the invention is for ultrasonic medical imaging. It allows an image to be obtained of a slice of tissue whenever there is involved an organ with a relatively homogeneous composition, which is the case particularly with the brain, breast and neck. It is also applicable to limbs since the high velocity zones are centrally located.

The invention will be better understood from the following description of particular embodiments, given by way of examples only.

SHORT DESCRIPTION OF THE DRAWINGS

FIG. 1 is a simplified diagram showing one possible arrangement of probes in a prior art apparatus, in the plane of the cross-section to be imaged;

FIGS. 2a, 2b, and 2c are simplified diagrams showing how the transmission and the reception are carried out in the case of a device according to the invention having slow scanning and without focusing;

FIGS. 3a and 3b, similar to the preceding ones, show how the transmission and the reception are carried out in the case of rapid scanning;

FIG. 6 is a simplified diagram of circuits for controlling the scanning and electronic focusing sequences, in an apparatus comprising a fast computer;

FIG. 7 is a simplified diagram showing how electronic focusing is carried out at transmission;

Figure 5:
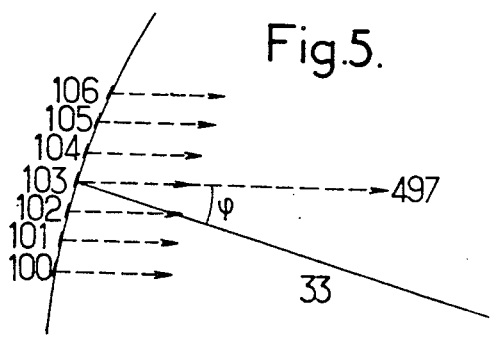
FIG. 5 is a simplified diagram showing how focusing is carried out.
Figure 8:
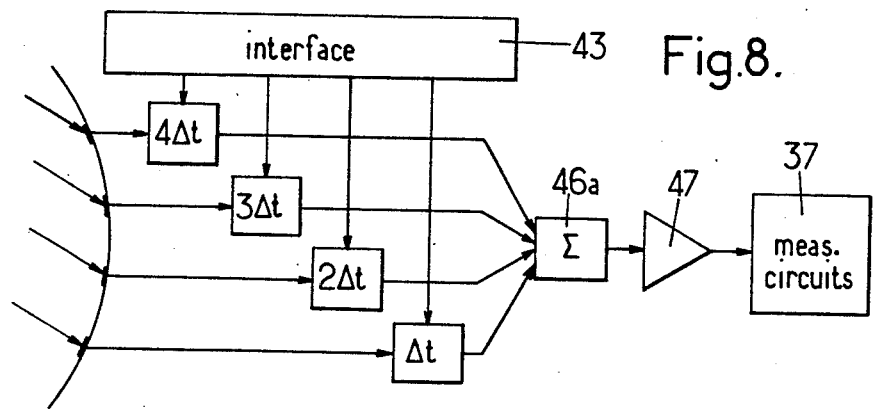
Figure 9:
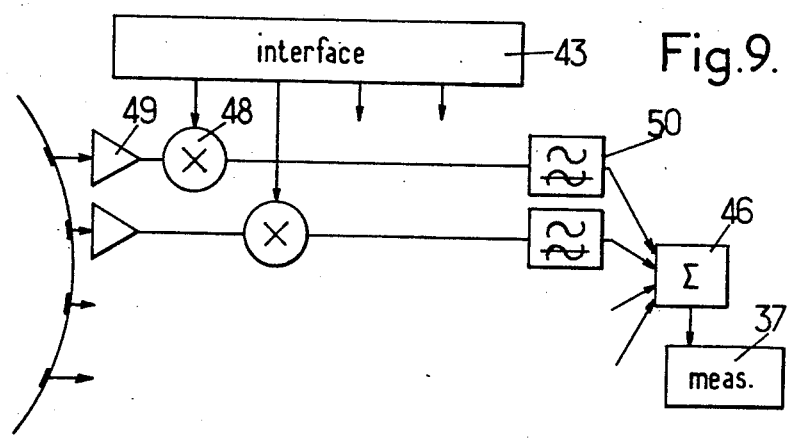
Figure 11:
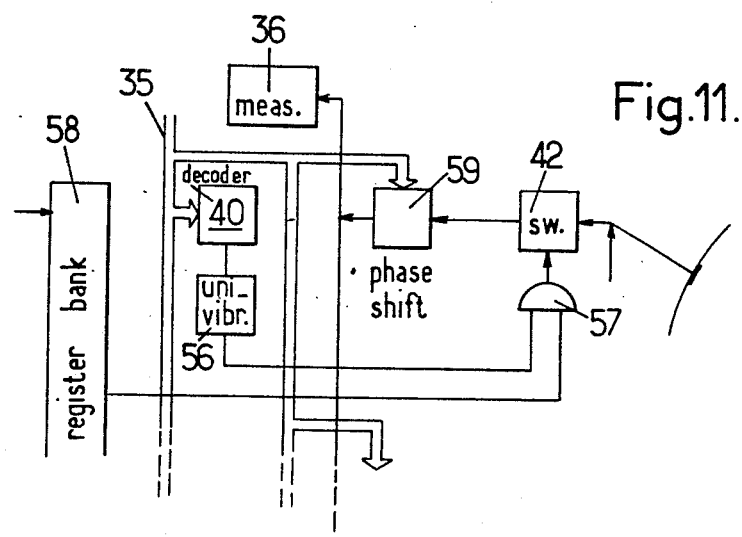
Figure 10:
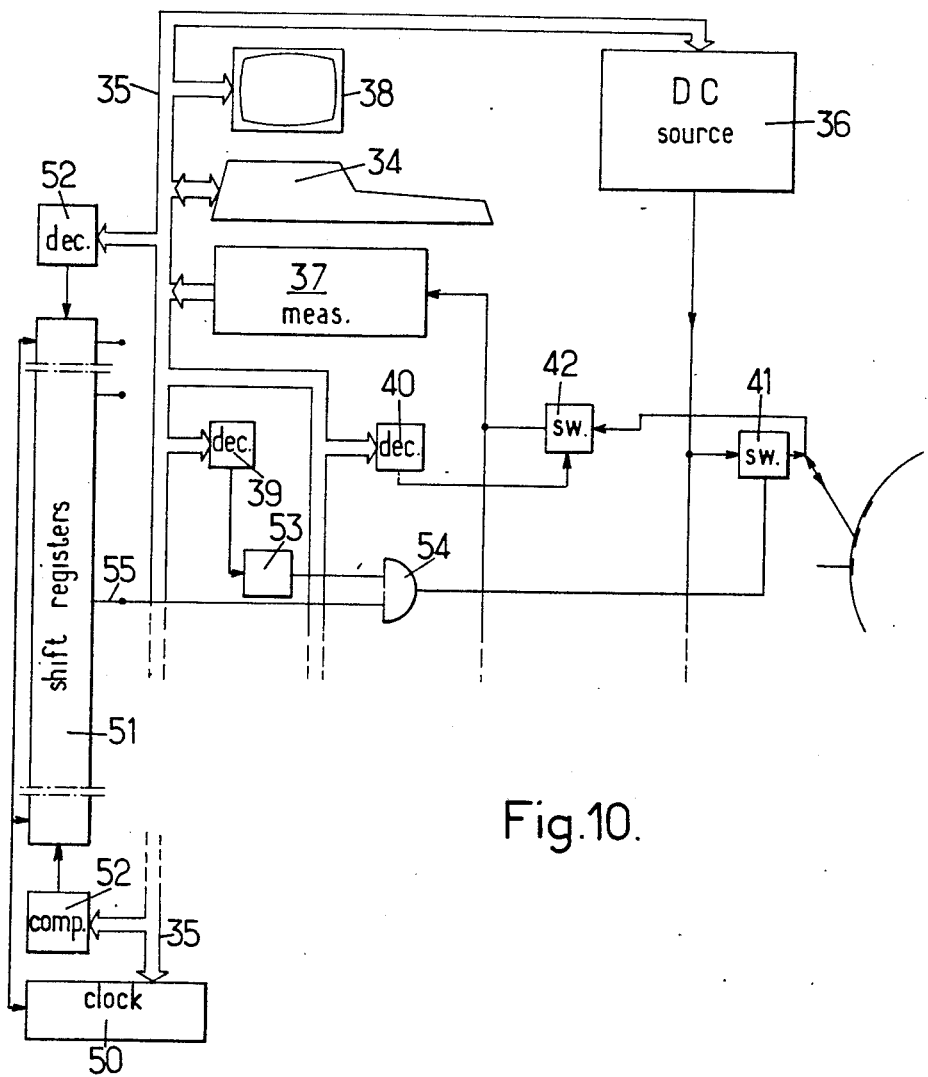
Figure 15:
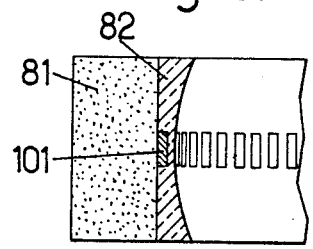
Figure 16:
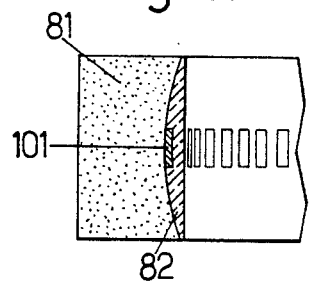
Figure 12:
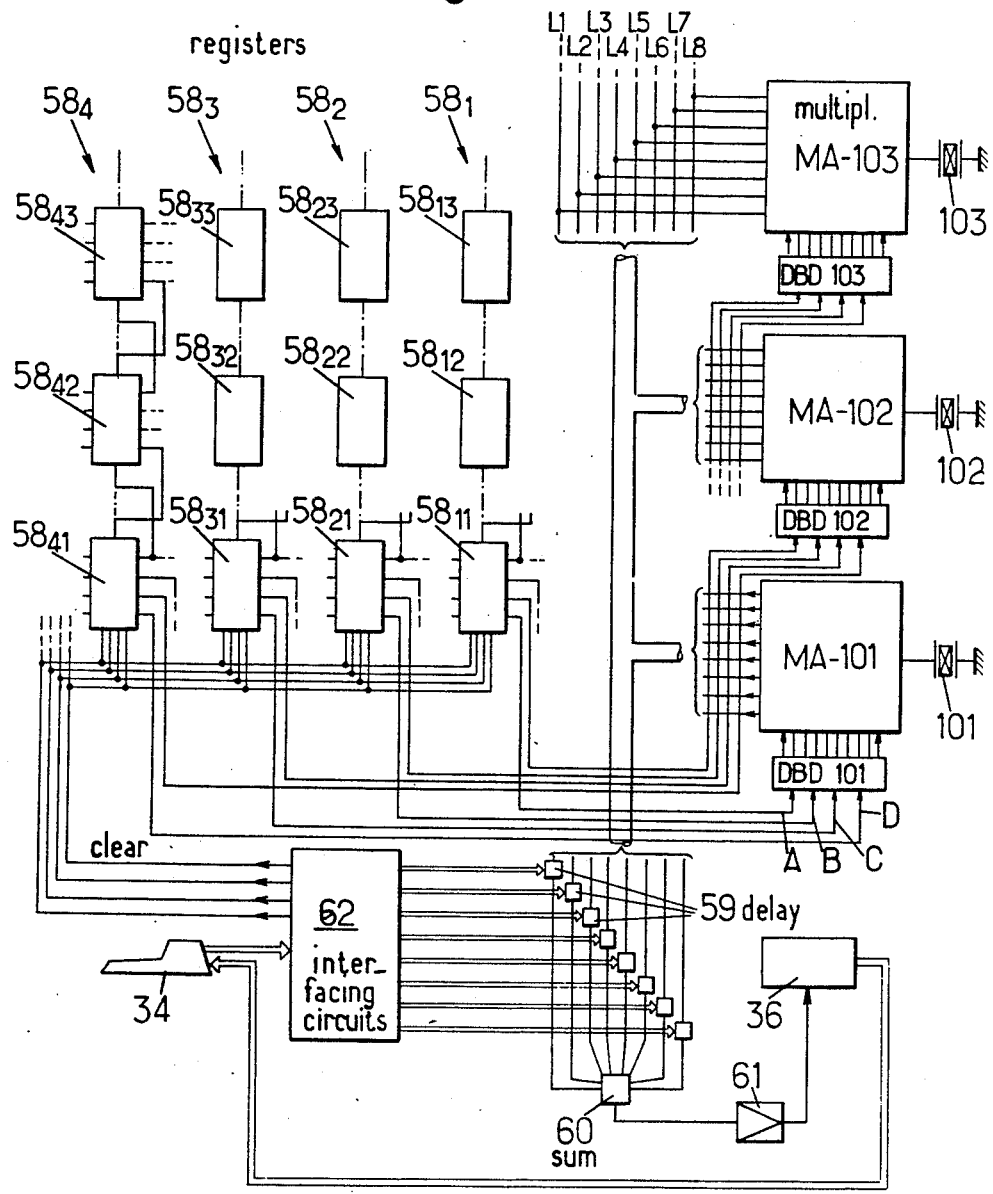
Figure 13:
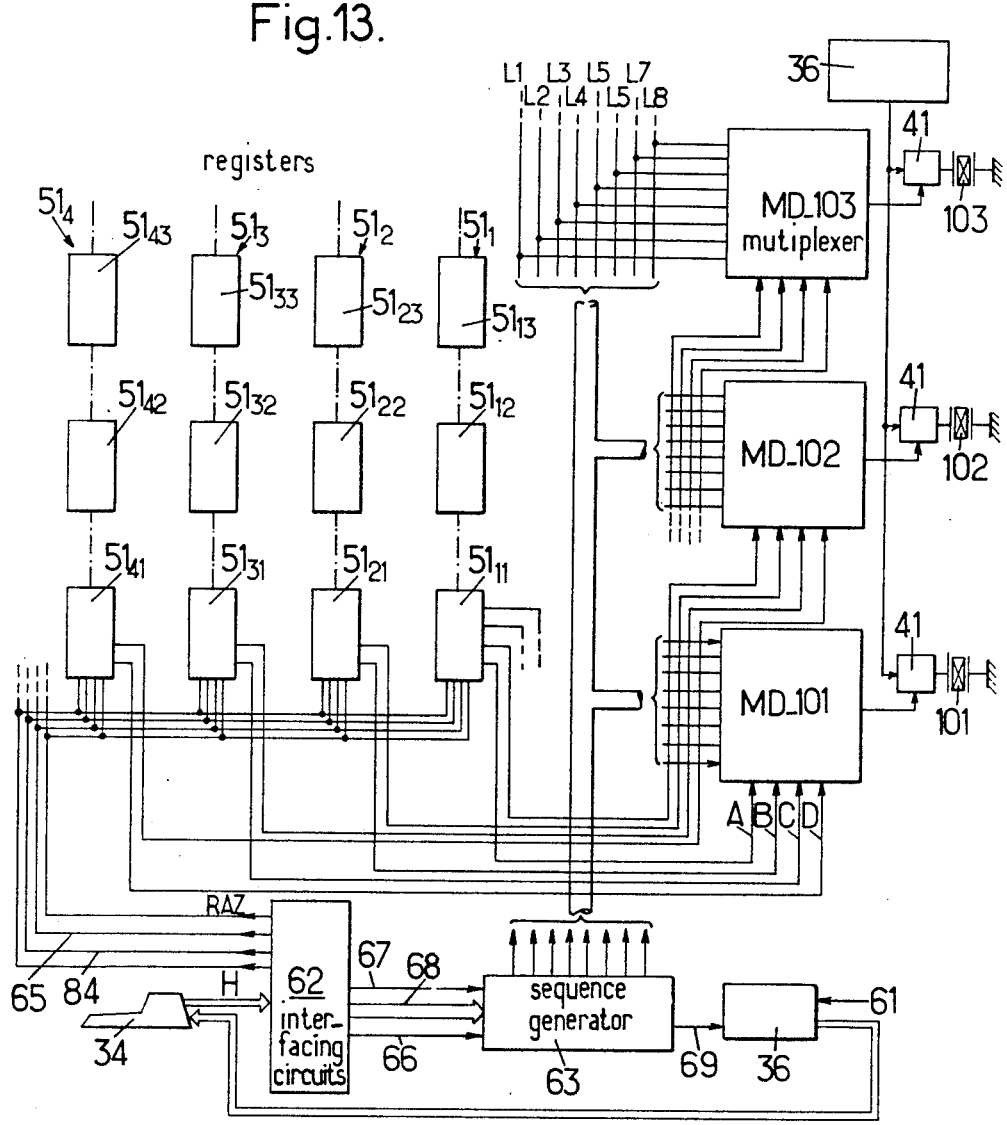
Figure 14:
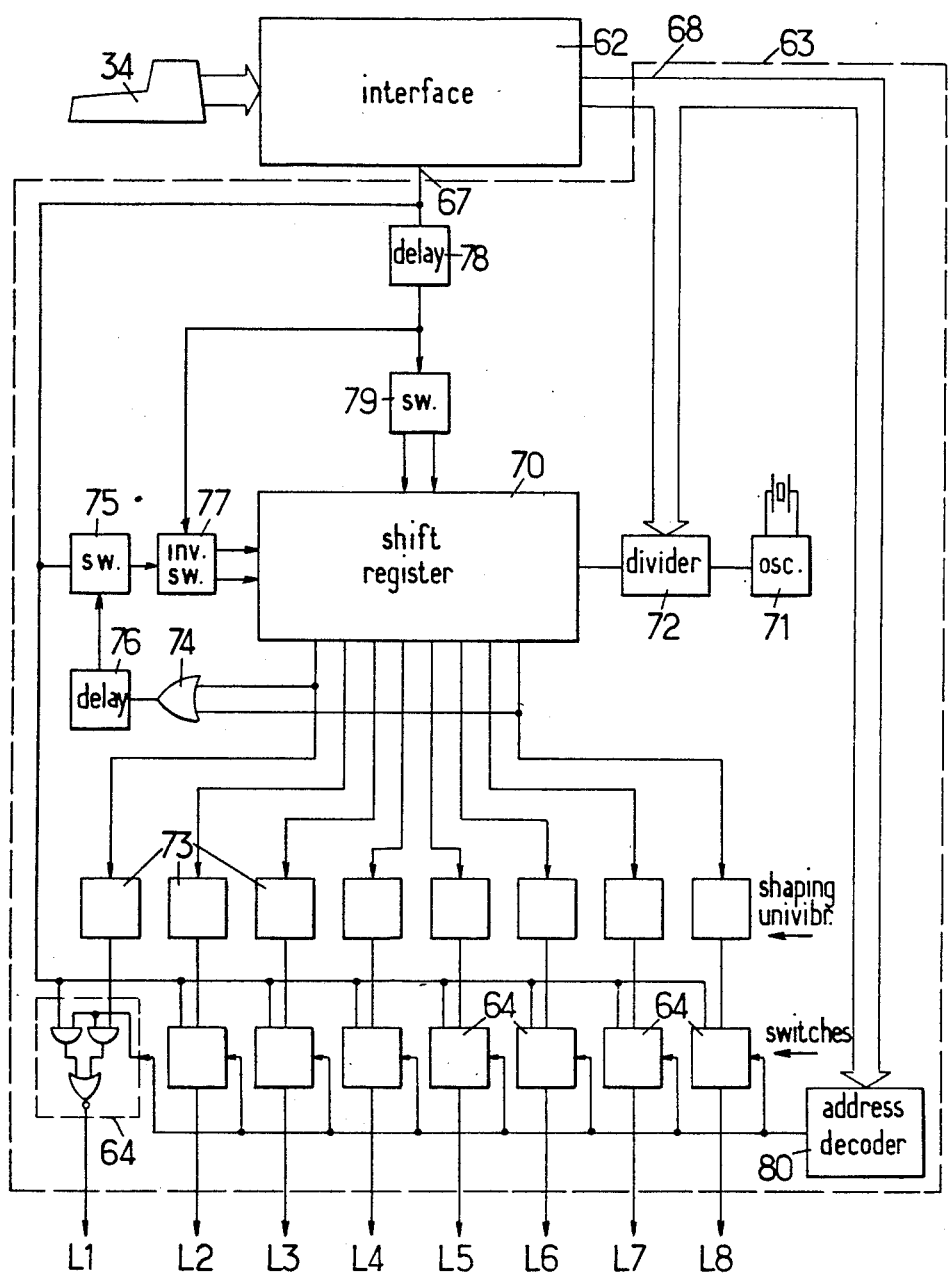
Figure 20:
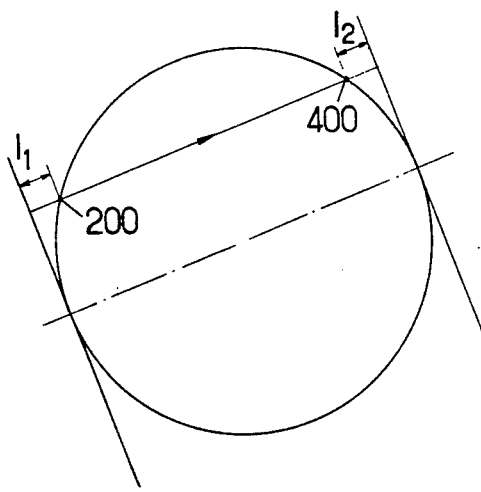
Figure 21:
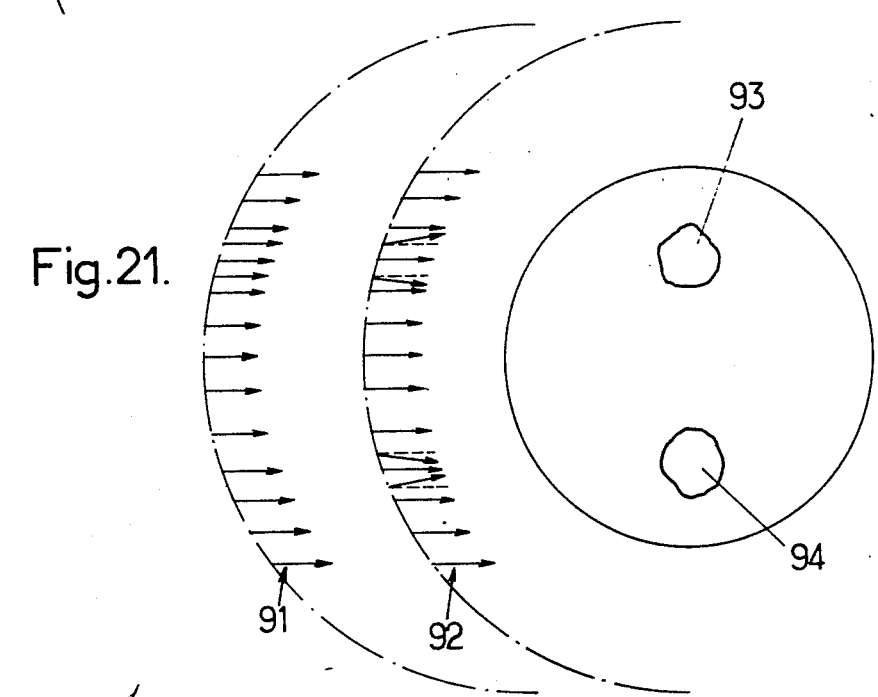
Figure 22:
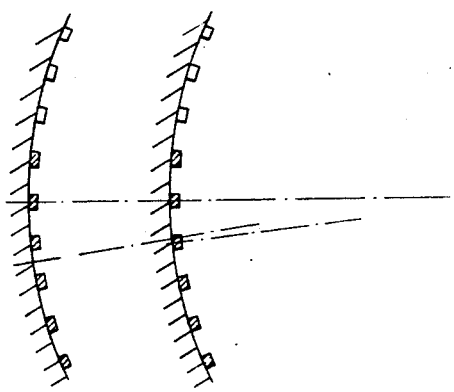
Figure 23:
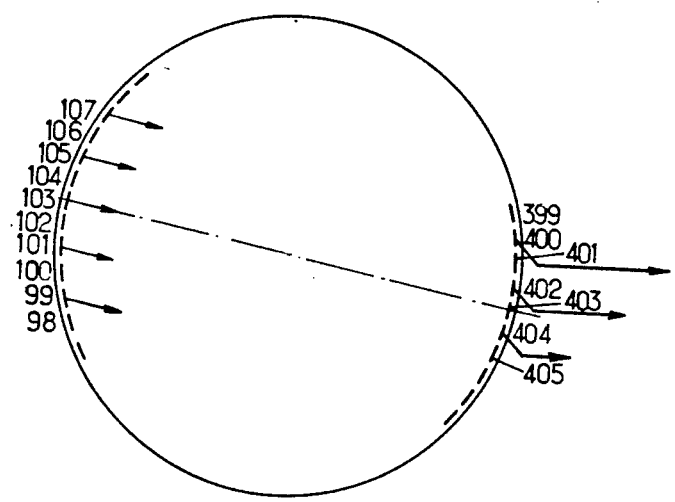

FIGS. 8 and 9, similar to FIG. 7, are simplified diagrams showing a method for focusing at reception;

FIG. 10, similar to FIG. 6, shows control circuits in an apparatus in which scanning is carried out by a programmed computer and electronic focusing by banks of shift registers;

FIG. 11 shows the components to be added to the reception circuits of a probe for achieving focusing at reception;

FIG. 12 shows in detail the construction of the switching and electronic focusing circuits at reception, incorporating banks of shift registers, analog multiplexers and mixers;

FIG. 13, similar to FIG. 12, shows in detail the switching and electronic focusing circuits at transmission, incorporating banks of shift registers and digital multiplexers;

FIG. 14 shows an embodiment of the sequence generator of the circuits of FIG. 13;

FIGS. 15 and 16 show schematically, in a section along a plane passing through the axis, one possible construction of the crown of probes, providing focusing in the sectional plane;

FIG. 17 shows schematically, in perspective, two fragments of the crown of probes providing focusing in the sectional plane at transmission and at reception, as well as the circuits directly associated therewith;

FIGS. 18 and 19 show very schematically, in perspective, sections of crowns of probes providing transmission over a large angular field in the sectional plane;

FIG. 20 is an explanatory diagram showing the need for flight time correction;

FIG. 21 is a simplified diagram showing how a refraction correction may be carried out;

FIG. 22 is a simplified diagram showing a process for increasing the resolution by alternating use of six and five probes;

FIG. 23, similar to FIG. 5, is an illustration of the operation of still another embodiment.

DETAILED DESCRIPTION OF PREFERRED EMBODIMENTS

Figure 1:
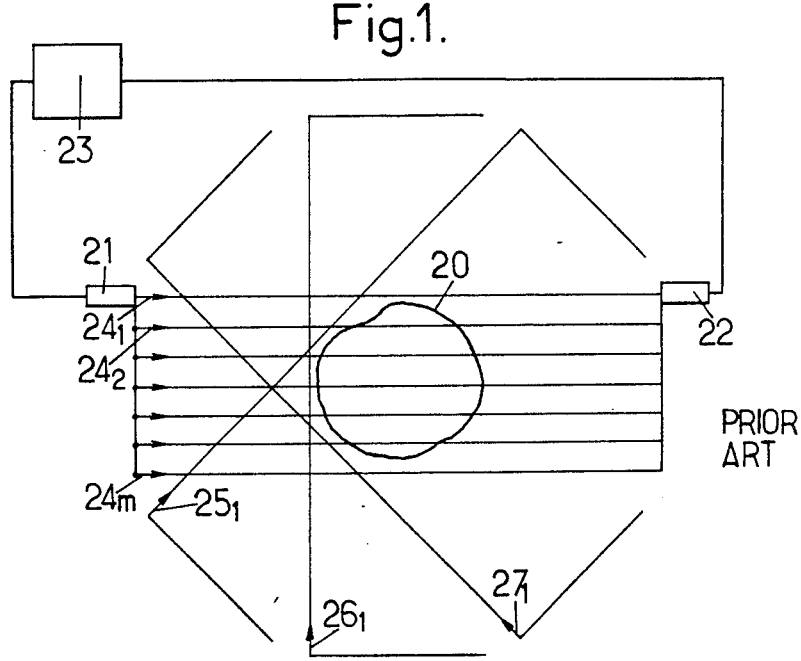

Referring first to FIG. 1, there is shown the construction of a prior art apparatus for transverse "axial" reconstruction tomography of an object 20 such as a portion of the human body. The apparatus comprises a transmitting ultrasonic probe 21 and a receiving probe 22 connected to an absorption or time-of-flight measuring and storage electronic circuitry 23. It comprises means for simultaneously moving probes 21 and 22. A first series of m measurements corresponding to m parallel paths $24_1, 24_2, \ldots, 24_m$ is carried out. Then one or more other series of m measurements each corresponding to m parallel paths is carried out; as illustrated in FIG. 1, three other series of measurements are carried out, corresponding respectively to parallel paths at $25_1$, to parallel paths at $26_1$ and to parallel paths at $27_1$.

Once the series of measurements are completed, a digital computer (not shown) reconstitutes the absorptions or speeds of the ultrasonic bursts at each point of the sectional plane containing paths 24, 25, 26 and 27. This reconstitution may be carried out by applying one of numerous well known algorithms. Such an apparatus and the operation thereof are described in J. F. GREENLEAF et al, already mentioned, which is included in the present specification by way of reference.

This apparatus requires mechanical movement whenever passing from one measurement to the next. This disadvantage is removed in the embodiments of the invention which will now be described.

All the embodiments which will now be described use probes distributed evenly at angular intervals around a circular mounting crown and it will be assumed, by way of example, that two successive probes are separated by an interval of 36', which corresponds to 600 probes on a complete circumference. The probes are formed by ceramic transducers, energized by low voltage pulses, allowing energizing transistors to be used which provide very accurate switching. These transducers may be moulded in an insulating resin crown. However, the probes may be distributed at equal linear intervals along several pairs of parallel strips, each probe being at one of the successive locations of the probe in FIG. 1.

Figure 2A:
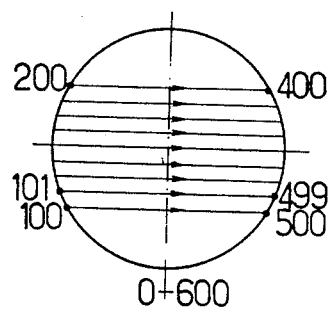
Figure 2B:
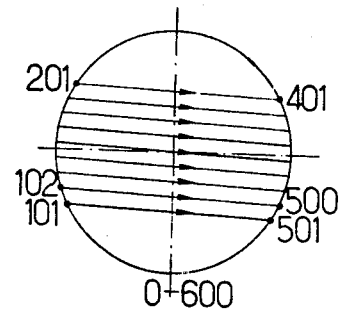
Figure 2C:
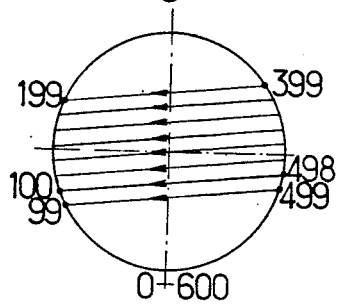

FIGS. 2a to 2c show the distribution of the probes and the fundamental operation of a first apparatus, which may be considered as an imaging apparatus operating in the slow mode, with electronic scanning, without focusing. On the other hand, a single multiplexed measuring channel only is required. Several successive series of absorption (attenuation) or time-of-flight measurements are carried out in sequence. During the first series of measurements (FIG. 2a), m measurements corresponding to m parallel paths are carried out. During the first measurement, a probe (probe No. 100 in FIG. 2a which illustrates an embodiment where m=101) is energized by an electrical pulse and delivers a burst of ultrasonic energy.

Probe No. 100 transmits energy over a wide angular field but the signal from one receiving probe only (probe No. 500) at a time is applied to the receiving channel and the corresponding data (representative of the absorption and/or time-of-flight) is stored in a memory.

Then probe No. 101 is energized by a pulse and the signal supplied by probe No. 499 is memorized, which corresponds to a path parallel to the preceding one, and so on up to the path between probes Nos. 200 and 400. It can be seen that thus there is obtained m=101 measurements during the series.

The second series of measurements is effected by shifting by one the probes which are used (FIG. 2b). Thus, there is obtained m=101 additional pieces of information corresponding to paths 101–501, . . . , 201–401.

The series of measurements are continued until the paths preceding immediately the paths reverse from those of the first series (FIG. 2c), i.e. paths 399–199, . . . , 499–99.

It can be seen that 16,000 measurements are required; at the rate of one measurement per ms, the complete scanning requires 16s.

Figure 3A:
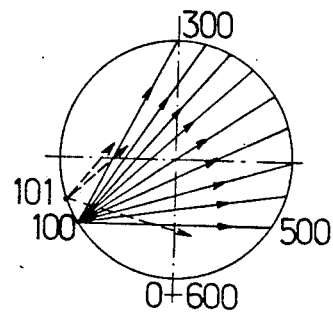
Figure 3B:
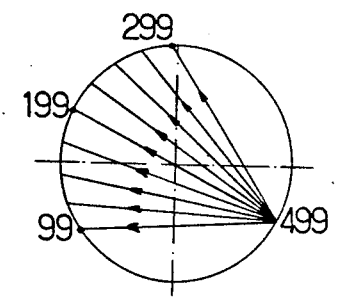

FIGS. 3a and 3b show the operation of a recording apparatus in a mode which may be qualified as rapid, without focusing, requiring m detection channels if there are m measurements per series, corresponding to m receiving probes. Each of the n series then comprises a single energization of a transmitting probe, but m simultaneous measurements by means of m receiving probes.

For example, the first series is carried out by energizing probe No. 100 (FIG. 3a) and collecting the signals supplied in reply by the m=201 receiving probes 300, ..., 500. Since the m signals are simultaneously collected and memorized, the apparatus must comprise m measurement channels.

For each subsequent series, the transmitting probe and the group of receiving probes are shifted by one until the configuration shown in FIG. 3b.

It can be seen that the number of series of simultaneous measurements is 200 and that complete scanning may be effected in 80 ms.

An apparatus may also be constructed operating in a mode which may be qualified as "semi-rapid": instead of providing m measurement channels, m/a are provided (a being a divisor of m) which requires a successive switching operations of the channels for each series of measurements from the same probe.

Figure 4:
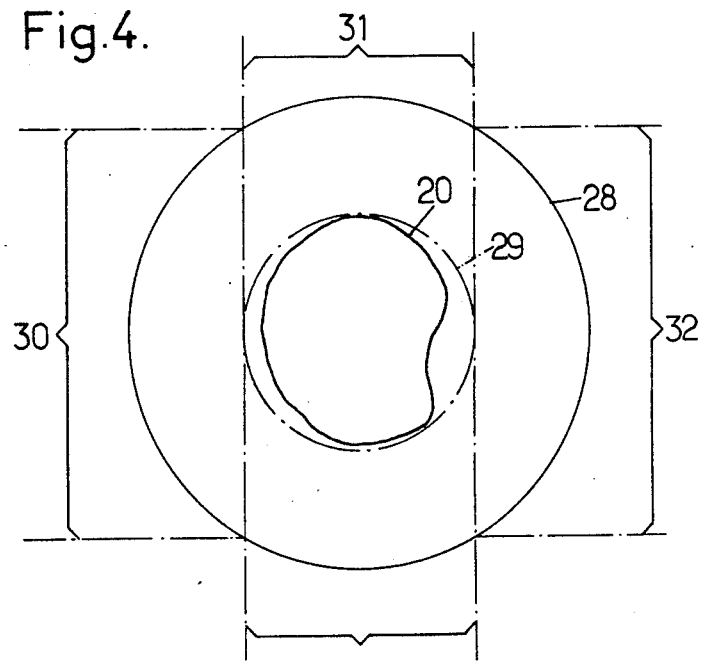
FIG. 4 shows a possible distribution of transmitting and receiving probes.

Whatever the mode adapted, in the absence of focusing, information (absorption and/or time-of-flight) corresponding to m×n paths will have been memorized, after all series of measurements. It will also be understood that it is not necessary to use all the probes successively at transmission or reception: as FIG. 4 shows, if the probes are distributed along a circle 28 and if the organ 20 to be studied fits into a circle 29, it is sufficient to provide transmitting probes in zone 30, transmitting and receiving probes in zone 31 and receiving probes in zone 32. Other distributions are obviously possible. In particular, if all the probes may be operated as transmitting and receiving probes, the recording of the measurements requires only scanning over 180°.

There will now be described, with reference to FIG. 5, the principle of the operation of a device in the slow mode, but with electronic focusing at transmission: this is an improvement of the operating mode shown in FIGS. 2a to 2c, for increasing the sensitivity of reception, so the signal/noise ratio, and for reducing the effects of multiple reflections and those of refractions in the object 20 to be studied.

To carry out energy focusing at transmission, instead of a single probe being energized for each measurement (for example 103), several probes (for example Nos. 100 to 106) are energized at the same time with time lags which cause an energy concentration along the suitable path (from 103 to 497 for example) forming an angle $\theta$ with the radius 33 passing through 103.

This time lag may be achieved in a simple way, by controlling the successive probes by means of pulses delayed by time intervals $\Delta t$, as will be seen further on.

The focusing of energy at reception may be based on the same principle as for transmission: to detect preferentially the energy arriving at an angle $\theta'$ in relation to the radius, it is sufficient to delay the signals from several receiving probes appropriately before summation of these signals. If for example attempt is made to detect preferentially the ultrasonic energy along path 103–497, elements providing delays 0, $\Delta t$, 2 $\Delta t$, ... are associated with probes 495–499 for the duration of the measurement and the outputs of the delay elements are connected to a summing circuit.

SWITCHING METHODS

The switching operations between probes will be more or less complex according as to whether a concentration of energy is effected by focusing. In all cases, switching may be achieved either by a computer which also serves for the reconstruction, or by a separate electronic circuit: three possible solutions are shown schematically, respectively in FIGS. 6, 7 and 8.

FIG. 6 shows a device for switching probes 0, ..., 599 using a computer 34. If focusing is not provided (case of FIGS. 2a–2c), a slow computer is sufficient, for example at 1 kHz, whose computing unit may be a microprocessor. If it is necessary to synthetize blocks of addresses to achieve electronic focusing at transmission, it is necessary on the contrary to have available a rapid computer (25 to 50 MHz).

Computer 34 is connected to an address bus 35 also coupled to a DC electric source 36 supplying the voltage required for operation of the probes (10 to 20 V in general), to a block of measuring circuits 37, to a display unit 38 (television monitor for example), to transmission address decoders 39 and to reception address decoders 40. Each of decoders 39 and 40, formed for example by an 8-bit digital comparator, is connected to a switching element 41 or 42. When a probe is provided only for transmission (or reception), it is provided with only one element 41 (or 42). It should be noted that alternate probes may be used, spread out over 360°, for transmission and reception. In this case, the first probes may be supplied with a voltage higher than the second.

The operation of such a device in the simple case of slow scanning is immediately apparent: the computer supplies successive pairs of transmission and reception addresses. Each pair is identified by a decoder 39 and a decoder 40 which enable the corresponding switching elements 41 and 42. Element 41 transmits from source 36 to the associated probe (103 for example) a short voltage pulse. Element 42 transmits the signal received by the associated probe (497 for example) to the measuring circuits which also memorize the information or transmit it, through channel 35 which then forms also the data bus, to computer 34.

As pointed out above, focusing at transmission is achieved by activation of several probes with a time lag. A fundamental circuit for achieving this result is shown in a simplified form in FIG. 7, where the elements corresponding to those in FIG. 6 bear the same reference numbers. An interface 43 interposes delay lines 44, 45, ... between the clock generator 46 (computer in the case of FIG. 6) and the switching elements 41.

At reception, a similar arrangement shown in FIG. 8 may be used; the probes are provided with variable delay lines, which may be the same as lines 44, 45, ... in FIG. 7, programmed by the interface 43. The outputs of the delay lines are summed at 46a. The resulting signal is amplified at 47, then applied to the block of measuring circuits 37. Instead of variable delay elements, synchronous detection mixers may be used to which are applied phase-shifted reference signals; the arrangement is then that shown in FIG. 9. The interface applies reference signals to mixers 48 which also receive the signals from the probes, after preamplification at 49. High-pass filters 50 remove the low frequency before summation at 46.

When it is desired to provide focusing at transmission, the solution shown in FIG. 6 has the disadvantage of requiring a fast computer. In another embodiment of the invention, a slow computer is used for scanning, electronic focusing then being provided by separate electronics. A portion of such an arrangement is shown in FIG. 10. The units of FIG. 10 corresponding to those of FIG. 6 are shown by the same reference numbers and will not be described again.

The electronic focusing circuit of FIG. 10 comprises a programmable frequency clock generator 50, a bank of reversible shift registers 51 comprising a number of binary positions equal to the number of probes used for focusing and two digital decoding comparators 52. Each of the decoders 39 drives the corresponding switching element 41, not directly, but through a monostable holding or latch circuit 53 and an AND gate 54 whose second input is connected to the output 55 of one of the positions of register 51. Computer 34 delivers successively a series of addresses corresponding to the group of transmission probes to be switched and this information is stored for a few hundred micro-seconds by the time-delay monostable circuits 53. The computer 34 then emits a transmission address, decoded by the comparators 52 and fed to the series inputs of the bank of two-direction series-parallel registers 51. A bit travels along the bank of registers at the clock frequency, fixed by the clock generator, in the required direction, so that the transmitting probes previously set up by the computer 34 are sequentially energized at clock periods. The same series of events is repeated, for example 1 millisecond later, for a group of different transmitting probes and for another clock frequency, corresponding to a different focusing angle, and so on up to the end of the scanning.

Focusing at reception may be achieved in the same way: FIG. 11 (where the elements corresponding to those of FIG. 10 bear the same reference numbers) shows schematically the components to be added to the reception circuit of a probe. Between the address decoder 40 and the switching element 42 are interposed a holding monostable circuit 56 and an AND gate 57 whose second input is driven by a stage of the register bank 58. A delay line and/or a programmable phase-shifter 59 addressable by bus 35 is inserted between the output of switching element 42 and the block of measuring circuits 36. The computer (not shown) or the address generator may be low frequency, since it does not have to synthetize the address blocks of all the switching elements required for the same focusing.

Delay lines or programmable phase-shifters are complex and expensive. There is then an advantage in reducing their number. This result may be achieved by multiplexing the receiving probes on delay lines or phase-shifters whose number is much less than the total number of probes.

FIG. 12 (where the elements corresponding to those of FIGS. 10 and 11 bear the same reference number) gives the diagram of an apparatus for focusing at reception with eight delay lines 59. Each receiving probe is connected by an analog multiplexer, MA 101 for probe 101 and so on, to eight outputs each connected to a programmable delay line 59. Delay lines 59 are connected to a summing circuit 60 so that only the signals received corresponding to a given focusing angle are added in phase before driving the measuring circuit through an amplifier 61. Lines 59 are programmed by the computer 34 through interface circuits 62.

The multiplexers MA are addressed and controlled from four banks of universal shift registers $58_1$, $58_2$, $58_3$, $58_4$. Each bank comprises 4 or 8 times less registers than there are receiving probes along the crown, according as to whether 4 or 8 bit registers are used. Bank $58_1$ controls the LSB of the number determining operation of the multiplexers MA, whereas bank $58_4$ controls the MSB. Each analog multiplexer MA comprises a binary-decimal decoder DBD 101, DBD 102, DBD 103, . . . allowing the registers to control it in four-bit binary code. The application of the binary word 0000 to one multiplexer disconnects the corresponding receiving probe by connecting it to the output o, not connected, of its multiplexer.

The groups of receiving probes are switched and focused as follows. The computer 34 (or a control circuit) adjusts from a proramme, for the predetermined focusing angle $\phi$, the values of the delays (or the phase shifts, or the phases of synchronous detection signals). If it is for achieving the first predetermined path, the banks of registers $58_1$, $58_2$, $58_3$, $58_4$ are cleared, then values preprogrammed by wiring of the support card or by software are loaded. These values are for example provided for controlling eight multiplexers MA so that probe 101 is connected to line L8, probe 102 to line L7, . . . , and probe 108 (not shown) to line L1. These prewired binary values are:

TABLE I

| Register (FIG. 12) | Word wired output No. 1 2 3 4 | Analog multi-plexer | Control applied to decoders DBD D C B A | Switched lines |
|---|---|---|---|---|
| $58_{11}$ | 0 1 0 1 | MX 101 | 1 0 0 0 | L8 |
| $58_{21}$ | 0 1 1 0 | 102 | 0 1 1 1 | L7 |
| $58_{31}$ | 0 1 1 1 | 103 | 0 1 1 0 | L6 |
| $58_{41}$ | 1 0 0 0 | 104 | 0 1 0 1 | L5 |
| $58_{12}$ | 0 1 0 1 | 105 | 0 1 0 0 | L4 |
| $58_{22}$ | 0 1 1 0 | 106 | 0 0 1 1 | L3 |
| $58_{32}$ | 1 0 0 0 | 107 | 0 0 1 0 | L2 |
| $58_{42}$ | 0 0 0 0 | 108 | 0 0 0 1 | L1 |
| $58_{13}$ | 0 0 0 0 | 109 | 0 0 0 0 | disconnected (L0 or L9) |
| $58_{23}$ | | 110 | | |
| $58_{33}$ | | 111 | | |
| $58_{43}$ | | 112 | | |

The electronic pulses received by the eight connected receiving probes are fed to the corresponding lines L1 to L8, delayed (or phase-shifted or mixed with a time variable phase reference signal) and added by the summation circuit 60.

On the transmission of a second ultrasonic pulse and before reception, the computer shifts the binary information by one position along the banks by means of the clock of registers 58, then modulates the delay lines 59 depending on the reception angle. Only receivers 102 to 109 are then connected, respectively to lines 1 to 8. The process is repeated until all the paths for the first tomographic recording angle $\phi$ have been scanned. The computer then reverses the shifting direction of the banks in accordance with an appropriate sequence and proceeds with recording a second series of scannings, for a second tomographic angle.

Since there are no readily available digitally programmable delay lines, synchronous detection may be used where the reference signal has variable time lag and phase (or frequency) synthetized for each line L1 to L8 and for each reception angle. The frequency of the reference signals may be synthesized from a surface wave delay line.

Switching and focusing at transmission may be achieved by means of the same arrangement as at reception: FIG. 13 (where the elements corresponding to those in FIG. 2 bear the same reference numbers) shows such an arrangement, in which the detection signals are synthesized by a sequence generator 63 used for the transmission signals and which will be described in detail further on with reference to FIG. 14.

Inverters 64 (not shown in FIGS. 12 and 13) allow the reception/transmission sequence generator 63 to be connected either to the digital transmission multiplexers MD 101, MD 102, . . . , or to the receiving probes, through analog multiplexers MA 101, MA 102, . . . (FIG. 12).

In order to achieve focusing and thereby enhance transmission, each transmitting probe may be connected to any one of eight lines L1, L2, . . . , L8 by its digital multiplexer MD controlled by one of the positions of one of the four banks of parallel loading universal registers. These four banks $51_1$, $51_2$, $51_3$, $51_4$ may be separate from banks $58_1$, $58_2$, $58_3$, $58_4$ or the same. Bank $51_1$ determines the LSBs at the input of the multiplexers MD, bank $51_3$ the MSBs. Bank $51_4$ controls the connection and the disconnection of the outputs of multiplexers MD, so that of the probes. The connections between registers are the same as in FIG. 12.

Switching interface 62 comprises, besides the connections with the address channel from the computer:

a low frequency clock output H (for example 1 kHz), an output RAZ for clearing registers 51, an output 84 whose level determines the shift direction in the registers, an output 65 for causing parallel loading of the registers.

All these outputs drive each of registers $51_{11}$ to $51_{43}$. The interface further comprises, towards the sequence generator 63:

an output 66 determining the direction of operation, an output 68 for supplying a transmission start signal, a bus 68 for transmitting words, of 18 bits for example, determining the frequency at which the ultrasonic bursts are emitted; these words may determine the dividing ratio applied to a predetermined frequency, for example 30 MHz or, better still, select one of a plurality of crystals and a ratio.

Generator 63, which essentially consists of shift registers, comprises, besides the outputs connected to lines L1 to L8, an output 69 for transmitting a measurement start pulse to the block of measuring circuits 36.

The switching of the multiplexers and the transductor elements takes place in the same way as at reception. Before recording the first path, the banks of registers are cleared. Binary words (predetermined by wiring) are then loaded in parallel into the registers through the parallel inputs thereof. These binary values may be different from those of the banks of reception registers, when the control of the digital multiplexers MD differs from that of the analog multiplexers MA used at reception.

If for example the digital multiplexers MD are 75 151 A multiplexers (TEXAS INSTRUMENT), the values of Table II ensure the switching and the focusing of the transmitters 101, 102, . . . , 108 on lines L8, L7, . . . for the first path.

In passing, it will be noted that, with software programming rather than wired memory, the computer 34 is connected by the data bus to registers 51 and 58. A separate loading channel for each register may furthermore be provided.

TABLE II

| Register | Word wired at parallel inputs 1 2 3 4 | Digital multiplexer | Control of the multiplexer D C B A L (enabling) | Switched lines |
|---|---|---|---|---|
| $51_{11}$ | 1 0 1 0 | MD 101 | 1 1 1 1 | L8 |
| $51_{21}$ | 1 1 0 1 | 102 | 1 1 1 0 | L7 |
| $51_{31}$ | 1 1 1 1 | 103 | 1 1 0 1 | L6 |
| $51_{41}$ | 1 1 1 1 | 104 | 1 1 0 0 | L5 |
| $51_{12}$ | 1 0 1 0 | 105 | 1 0 1 1 | L4 |
| $51_{22}$ | 1 0 1 0 | 106 | 1 0 1 0 | L3 |
| $51_{32}$ | 0 0 0 0 | 107 | 1 0 0 1 | L2 |
| $51_{42}$ | 1 1 1 1 | 108 | 1 0 0 0 | L1 |
| $51_{13}$ | 0 0 0 0 | 109 | 0 0 0 0 | MD disconnected |
| $51_{23}$ | 0 0 0 0 | 110 | 0 0 0 0 | MD disconnected |
| $51_{33}$ | 0 0 0 0 | 111 | 0 0 0 0 | MD disconnected |
| $51_{43}$ | 0 0 0 0 | 112 | 0 0 0 0 | MD disconnected |

The sequence of operations for scanning the other paths is similar to that used at reception. There is: shifting of the contents of the registers in the appropriate direction under the control of the computer 34; writing, in the registers of the sequence generator 63, of the sign and modulus of the focusing frequency; finaly, transmission of a sequence of ultrasonic bursts by the eight transmitting probes switched by banks $51_1$ to $51_4$.

FIG. 14 shows schematically an embodiment of the sequence generator 63. The generator shown comprises an eight-bit twin-direction series-parallel shift register 70 and a clock frequency generator comprising an oscillator 71 (for example 25 MHz) and a digital frequency divider 72 (for example 18 bits). The frequency divider 72 and the oscillator are controlled by a binary word stored in the registers of the control interface 62. The outputs of register 70 are connected, by means of shaping monostable circuits 73 providing square wave pulses of constant width and independent of the clock frequency, to the digitally controlled inverting switches 64. Since the transmission order pulse delivered on the output 67 by interface 62 is not synchronous with the variable frequency clock pulses, t there is provided a circuit for inhibiting this pulse for a period of a few hundred microseconds from the first transition appearing on line L1 or L8. This circuit comprises an OR gate 74 driven by the outputs of register 70 to lines L1 and L8 and whose output controls a switching element 75 through a delay circuit 76 such as a monostable circuit. The switching element 75 is inserted between the output 67 and the data input of an inverting switch 77 whose outputs are connected to the right and legt serial inputs of register 70. The control input of switch 77 receives the signal from output 67 through a delay element 78 which controls a second switch 79 for selection of "right hand mode" and "left hand mode" of register 70. Due to the inhibition circuit, a single pulse is sent to each monostable circuit 73 for each transmission order at output 67.

Finally, channel 68 drives, in addition to divider 72, an address decoder 80 controlling switches 64, which may be dispensed with if the computer interface has a control bus.

The operating sequence is the following;

clearing of the parallel-parallel registers 70, loading of the frequency division ratio corresponding to the required clock frequency and so to the desired focusing angle, in binary form, into divider 72, selection and storage of the transmission direction of the sequence (storage by time delay in the illustrated embodiment), transmission of a pulse for triggering the transmission sequence which is directed to that one of the serial inputs of the register which has been selected by interface 62 (right or left).

If several crystals are provided, they can be selected by means of the control bus of the interface (4 bits for example).

For very small focusing angles requiring a clock frequency greater than the maximum frequency of the register, interface 62 displays a binary number which is decoded by a digital comparator which then connects all the outputs L1 to L8 to a single source of pulses, which corresponds to transmission with a zero deflection angle.

CONSTRUCTION OF THE PROBE CROWN

The probes must be held rigidly and accurately in place. They may be placed in a polygon (so as to obtain, but without any mechanical scanning, the same results as with the arrangement of FIG. 1). However, it will be more advantageous to give them the circular distribution shown in FIGS. 2 and 3. This arrangement is particularly advantageous when the section of the body to be studied has an approximately circular shape: this is the case when the apparatus is for ultrasonic imaging of a section of a breast, intended to reveal the zones where the absorption or the speed of the ultrasounds is abnormal. In this case, the coupling between the tissues and the probes will generally be provided by a water bath whose temperature is tied to that of the tissues and in which the crown is immersed.

The probes are then carried by an annular block of synthetic resin, which may be constructed from several elements (five for example) each having a small angular extent, then assembled by moulding, for example with "Araldite".

A same block may comprise several superposed crowns of probes, which allows, without moving the block, several parallel sections to be made successively or simultaneously.

Whether the device provides concentration of energy at transmission and/or at reception or not, it is desirable that the ultrasonic energy be transmitted in the form of a lobe as narrow as possible in the direction perpendicular to the sectional plane an image of which it is desired to obtain: focusing must then be sought in the axial direction.

For frequencies of a few MHz (typically 4 MHz) which will be generally used, this result may be achieved either optically, or by association of the transmission from several transducers.

FIGS. 15 and 16 show schematically a fraction of two probe crowns such as 101 providing optical focusing. In FIG. 15, the probes are placed on the internal face of a damping block 81 in a crown, and embedded in an annular insulating support 82 whose internal face is concave, so that if forms an annular convergent lens. In FIG. 16, it is the internal face of the damping block which is concave and the probes have a curvature in the sectional plane.

FIG. 17 shows two fragments of a probe crown providing focusing by composition at transmission and reception. Each probe comprises several elementary transducers 83, 85, 86 disposed symmetrically in relation to the sectional plane. It can be seen that the transducers of probe 101, used as a transmitter, are connected to the source 36 by a single switching element 41 and delay lines or suitable phase shifters 87 and 88. Switch 42 of probe 499 used as a receiver receives the signals of the transducers through corresponding phase shifters 87' and 88' and a summing circuit 89. Thus can be obtained a beam whose focused zone in the sectional plane has substantially the same dimension as the length of the transducers; there is thus obtained a collimated beam of small thickness.

When the device is for carrying out scanning in fast mode (FIGS. 3a and 3b), or for concentrating energy (FIG. 5), the probes of a crown must transmit in considerably angular fields of the sectional plane, up to for example ±30° (the field being all the greater the larger the radius of the useful zone of the crown). This fan-like shape, not only at transmission but also at reception, imposes a limitation of the circumferential length of the probes, i.e. their width. Another method, illustrated in FIG. 18, consists in locating in front of each transducer a small cylindrical divergent lens 90. Yet another method consists in shaping the inner face of ring 82 so as to obtain these lenses. The probes may, finally, be given the shape of a half-tube (FIG. 19).

MEASURING AND COMPUTING CIRCUITS

It has been pointed out above that the device must effect measurements of absorption and/or of time-of-flight (it being understood that additional measurements may be made).

The measurements thus made are fed to the computer which will be able to provide an image of the distributions of one or the other in a section or an image resulting from a combination of the two measurements. The following displays may typically be used:

display of the cross-section in the form of an indication of the absorption (A) or the velocity of the sound (B) at each point;

display of the diffusion spectra;

combination of these techniques, in the form for example of A+B, A×B, log A+log B, A in one colour and B in another, F(A)+F(B), F(A,B), (F being any predetermined function).

Attenuation is measured in a conventional way: the measuring circuits comprise, for each channel, a rectifying circuit giving the amplitude of the wave, or a circuit or Fourier transformer giving the value of the signal received which may be compared with that of the signal transmitted or, more frequently, considered as an absolute value, subject to standardization corrections which will be described further on.

The measurement of the propagation time (time-of-flight) may be made by taking into account the attenuation of the beam or not. In practice, the two magnitudes may be advantageously linked.

For example, for a not too high amplification gain and for a low signal/noise ratio, the times of flight for signals attenuated too much by the object will preferably not be taken into account for the measurement, whereby the refraction effects are reduced. A tomogram of the times of flight taking into account also the attenuation information will enhance the results by giving much weight to axial propagation directions of the beam.

Different methods are suitable for measuring propagation times with sufficiently accuracy, rapidly and automatically. For example, the electric pulse from the receiver may be digitalized and stored in a computer which then determines the propagation times by means of one of the appropriate algorithms. Also, if fast acquisition is desired, the propagation time may be measured by means of a counter fed by a clock, triggered by the transmission pulse and stopped by the reception pulse. Thus, the time of flight is obtained in digital form and recorded by the computer.

The existing processing algorithms apply to signals supplied by an arrangement of the kind shown in FIG. 1. Before processing the data recorded by the circular crown, it is advisable to apply thereto a geometric correction so as to be able to use the existing tomographic reconstitution algorithms. The correction consists in adding, to the time of flight measured by the crown, along for example a path 200–400 (FIG. 20), the time of flight which a pulse being propagated over the path $l_1+l_2$ would have. When the apparatus is used for imaging soft organic tissues immersed in water at the same temperature forming the coupling liquid, this additional time of flight is computed from the distance $l_1+l_2$ and the speed in water corresponding to the temperature thereof.

Then the tomographic reconstruction algorithm may be similar to those in conventional methods (FIG. 1).

Furthermore, the reconstruction algorithm may take into account the variation of spacing between the successive parallel paths which are not quite equidistant, since the transducers are spread out at equal angular distances along a straight line.

For most cases, there will exist differences between the energies transmitted by and the reception sensitivity of the probes. There will also be differences of propagation time between two pairs of probes which have the same theoretical spacing.

These differences may be substantially reduced by constructing the probes from elements cut from the same ring of transducer material, having the same radius as the crown. At the same time, the surface limited by the probes is made more exactly circular and so the constancy of the times of flight between transducers separated by the same theoretical distance. However, it is still desirable to effect a correction so as to take into account these imperfections of measurement, by storing, in the memory of the computer, attenuation and time of flight corrections for each pair of probes or group of probes used in the measurements. These corrections can moreover be permanently adjusted depending on the temperature of the coupling water, for example by measuring the speed of the waves between two probes.

PHYSICAL CONSTRUCTION

There will now be described a particular embodiment for ultrasonic imaging of a breast.

The apparatus comprises a table provided with a recess placed at the level of the chest of the patient and under which is disposed an immersion tank filled with water. The tank is provided with a device for adjusting the temperature of the water, which is required both for comfort and for reducing refraction errors. The crown of ultrasonic probes (or several crowns of superposed probes) is supported by a mechanism for moving the probe, laterally and in depth while it is immersed. Another solution consists in placing the crown in contact with the breast through a coupling product having suitable properties.

The electronics for switching and possibly focusing, the measuring circuits, the computer and the interface are grouped close together and connected by wires to the crown.

The device is completed by a display unit which generally comprises a CRT with memory providing grey levels or a CRT without memory but provided with a digital memory for periodic refreshing.

In this application, numerous corrections may be contemplated for increasing diagnostic reliability and accuracy.

Refraction corrections: The refraction of the waves used for the tomographic imaging deflects them on the one hand at the interface between the immersion liquid and the object to be examined (circular dioptre for the breast), on the other hand, inside the object itself because of the refraction index variations of the tissues.

The first effect may be minimized by locating the crown in close proximity to the object and by controlling the ultrasonic speed in the bath for identity with the average value in the tissues; it may even be eliminated by using a crown in contact with the object.

To correct the second effect, an iterative process must be used, shown schematically in FIG. 21. A first recording is effected, followed by a first tomographic restitution. The speed values reconstructed from the first recording (corresponding to the maximum transmission directions shown at 91) are used to modify the electronic focusing and/or the reconstitution algorithm, so as to form a new image with slightly different transmission directions (at 92 for example) and so on.

An example of focusing modulation reducing the refraction effects in the tissues is described in FIG. 21. The process uses a function of the time of flight profiles of the first recording, (for example the spatial derivative), to modulate, during a second recording, the ultrasonic transmission and reception angle (obtained by electronic focusing).

In this example, the angle is all the more modified if the derivative of the profile has a higher value and in a direction varying with the sign thereof. In other words, the device should cause the beams emitted to diverge when a zone of the object tends to cause them to converge (low speed zone 93) and vice-versa (high speed zone 94).

This modulation of the focusing depending on zones of the object may be made linearly; it may also, for certain regions, be programmed in the computer.

Temperature correction: The temperature of the immersion bath is regulated to a value ensuring the comfort of the patient; it is desirable to make different automatic corrections of the recorded data if it is not sufficiently accurate:

geometry corrections depending on the temperature of the bath;

standardization correction of the probes depending on the temperature of the bath;

recording standardization correction at the temperature of the bath;

adjustment of the transmission and reception electronic focusing control depending on the temperature of the bath.

The values of the temperature and of the sound speed in the bath and in the tissues examined may be deduced from measurements between the probes of the crown by using propagation time information when passing ultrasounds in the bath and the tissues and when reflecting waves from the object examined.

If the regulation of the temperature is carried out with sufficient accuracy, it renders servo-control of the geometry corrections and others useless, since they may then be considered as constant and permanently stored in the computer. However, to minimize the refraction effects at the dioptre formed by the coupling liquid-object interface (circular dioptre in the case of the breast), it is desirable to servo-control the ultrasonic velocity in the bath as a function of the average ultrasonic velocity in the object. This control is achieved by controlling the temperature from information collected at intervals on the following parameters:

(a) ultrasonic propagation time in the bath between two probes without interpositioning of the object;

(b) average of several times of flight taken between a large number of probes for paths passing through the object at different angles;

(c) dimensions of the object for the paths considered in (b), by echography using the crown.

Numerous embodiments of the invention will be apparent and now be briefly mentioned.

The resolution may be increased by the following process, also applicable for the use of the crown in electronic scanning composite echography: if N is the number of transducer elements distributed evenly along the circumference of a crown, the angular separation between two paths (influencing the limit resolution) is 180/N degrees. In other words, the minimum displacement of the transmitter and the receiver in electronic switching spatial sampling is at least $\pi D/N$ (D being the diameter of the crown). This separation may be reduced, so the resolution increased, by alternatively using two groups having a number of probes different by one for electronic focusing, for example by using alternatively 6 and 5 probes. The sampling pitch of the electronic switching is then halved, as shown in FIG. 22.

This modulation of the number of probes is accompanied by modulation of the intensity of the wave emitted or of the reception sensitivity. For measuring the times-of-flight, this modulation has only a low incidence. It may be corrected in an attenuation measurement.

Instead of using conventional digital processes of tomographic reconstitution, analog processes may be used (electronic and optic) by formation of data and filtering of the spatial frequencies in proportion to their modulus (Peter's process).

In yet another embodiment of the invention, the crown of probes records echograms of the object to display a slice thereof or to use the information for correcting axial tomograms.

Then operation is as follows. The same group of probes is sequentially energized at transmission and at reception to achieve focusing. By varying the deflection and focusing angle, the group of probes emits a pulse and receives echoes reflected for different lines of the compound echogram, in an angular field of limited value. By changing the group of transmitter-receiver elements, another series of lines of the echogram is recorded in the same way, and so on until 360° have been covered.

Moreover, the profile of the two-dimensional ultrasonic velocity distributions obtained by means of the crown by calculated axial tomography supplies information which may be used for correcting the aberrations of such a wide aperture echogram.

In yet another embodiment of the invention (not shown), focusing is achieved in a mode which may be qualified as semi-rapid: two simultaneous scannings with focused transmission are typically effected simultaneously by using two ultrasonic beams whose directions are at 180° to each other, without appreciable interference; such a construction however involves the use of transmitting and receiving probes which are distinct and interleaved. The number of simultaneous scannings may be increased, but it seems difficult to exceed four without interference between the measurements.

In a modification of the embodiment with semi-rapid scanning, illustrated in schematic form in FIG. 23, each of the focussed transmiitted beams is formed by a plurality of transmitting probes whose number is selected for the beam to have an angular extent corresponding to several receiving probes. Referring to FIG. 23, one of the beams is formed by five transmitting probes 99, 101, 103, 105, 107 and the transmitted energy pulse is detected by three receiving probes 400, 402, 404 each associated with a separate measuring circuit. That arrangement requires as many circuits as there are receiving probes which are simultaneously used, but increases the scanning speed. Since there are separate and distinct probes for transmitting and receiving the pulses, scanning should be throughout 360°. It has been found this is frequently of advantage as regards the effects of refraction and diffraction.

The invention makes it possible to display the zones of the sectional plane in which there is a flow, if they are localized and well differenciated: such conditions are fulfilled for the neck. The processing of the signals received is then as follows:

the presence of a Doppler frequency signal is detected in each signal suplied by a probe or a group of probes, the signal is compared with a threshold to obtain binary information (presence or absence), the stored information is processed according to an axial tomography algorithm to obtain a binary representation, for example in black and white; the algorithm may be a summation algorithm, followed by spatial filtering.

For this application to the neck, a flexible coupling collar may be used, in one or more parts, placed between the crown and the tissues.

We claim:

1. A ultrasonic image reconstruction tomography apparatus for passing ultrasonic energy bursts in a transverse cross-sectional plane of an object and reconstructing the two-dimensional distribution of the values of at least one parameter of said object, comprising:

a plurality of ultrasonic energy probes distributed at substantially equal angular intervals along a crown having an axis arranged to be placed perpendicularly to said cross-sectional plane, means for generating successive electric pulses, means associated with said pulse generating means and with said probes for applying each said pulse to a group of said probes including a central transmitting probe and adjacent transmitting probes, said associated means including focusing means arranged to pass said pulse to the adjacent transmitting probes with time delays to provide focussing of the energy in a particular direction such that said group of probes delivers an ultrasonic burst in the form of a beam directed toward and having a focal point at least one associated probe diametrically opposed to said group of probes, receiving means connected to said probes for collecting signals received by said at least one associated probe in response to each burst passed through said cross-sectional plane from one said group of probes, scanning means for changing one at least probe of said group of probes connected to receive said pulse and for changing said at least one associated probe connected to the receiving means after each burst, memory means for storing the successive signals collected by said receiving means, and means for reconstructing the distribution of the values of said parameter in said cross-section by processing the stored signals, whereby reconstruction is achieved from the measurements on said beams directed at different angles in the cross-sectional plane without moving the probes.

2. Apparatus according to claim 1, wherein said receiving means are constructed to measure the time of flight in said object and means are provided for correcting differences of path between transmitting and receiving probes during successive measurements.

3. Apparatus according to claim 1, wherein said scanning means are arranged and connected to bring each time into play a different system comprising a group of transmitting probes and at least one receiving probe by associating the latter with a measuring channel.

4. Apparatus according to claim 1 or 3, wherein said scanning means simultaneously bring into play at the same time n transmitting probes, distributed at equal intervals along said crown, whereby they simultaneously emit beams along directions which are distributed angularly, coupled by n ultrasonic beams to n receiving probes by associating a separate measuring channel with each of the latter probes, the transmitting and receiving probes being interleaved along the crown.

5. Apparatus according to claim 1, wherein the scanning means are constructed and arranged for causing simultaneously transmission of at most four ultrasonic beams, from transmitting probes of said group of probes located at equal angular intervals on the crown.

6. Apparatus according to claim 1, wherein said scanning means operate simultaneously m receiving probes corresponding to said at least one associated probe (m being a predetermined integer) by associating each of said receiving probes with a separate measuring channel.

7. Apparatus according to claim 6, wherein means for reception focusing are arranged to connect a same measuring channel to a said receiving probe and to adjacent probes with a phase shift or time delay corresponding to selective reception of the energy arriving from the direction of the transmitting probe.

8. Apparatus according to claim 7, wherein the adjacent probes are even in number and placed symmetrically in relation to the first one.

9. Apparatus according to claim 7, wherein the scanning and focusing means are provided for bringing alternately into plan an even number and an uneven number of probes so as to improve the resolution.

10. Apparatus according to claim 6, wherein the scanning means comprise an address decoder and a switch associated with each probe and a digital computer which supplies successively the addresses of the decoders corresponding to the groups of probes to be brought into play at transmission and at reception.

11. Apparatus according to claim 10, wherein said focusing means comprise a shift register provided with a clock generator which causes a bit to circulate in the register when it is controlled by the computer, and a gate associated with each switch, connected to one stage of the register and only allowing the corresponding probe to be brought into service when it is enabled by the presence of the bit in the corresponding stage.

12. Apparatus according to claim 11, wherein each probe is provided with a multiplexer addressable by software.

13. Apparatus according to claim 10, wherein each probe is provided with a multiplexer addressable by a bank of said registers.

14. Apparatus according to claim 10, wherein the computer comprises computing means for correcting the propagation time and/or the ultrasonic attenuation coefficients from stored data and from the signal supplied by a probe measuring the bath temperature.

* * * * *